United States Patent
Scheirlinck et al.

(10) Patent No.: US 11,485,562 B2
(45) Date of Patent: *Nov. 1, 2022

(54) RESPIRATORY EQUIPMENT PACKAGING AND A PACKAGING INSERT FOR RESPIRATORY EQUIPMENT

(71) Applicant: Fisher & Paykel Healthcare Limited, Auckland (NZ)

(72) Inventors: Erik Robertus Scheirlinck, Auckland (NZ); Neil Gray Duthie, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/213,018

(22) Filed: Mar. 25, 2021

(65) Prior Publication Data

US 2021/0276781 A1 Sep. 9, 2021

Related U.S. Application Data

(63) Continuation of application No. 16/085,990, filed as application No. PCT/NZ2017/050026 on Mar. 17, 2017, now Pat. No. 10,988,299.
(Continued)

(51) Int. Cl.
*B65D 77/26* (2006.01)
*A61M 16/06* (2006.01)
(Continued)

(52) U.S. Cl.
CPC ......... *B65D 77/26* (2013.01); *A61M 16/0683* (2013.01); *B65D 31/12* (2013.01);
(Continued)

(58) Field of Classification Search
CPC .......... A61M 16/0683; A61M 16/0694; A61M 2209/06; B65D 31/12; B65D 33/2591; B65D 77/26; G09F 5/042
(Continued)

(56) References Cited

U.S. PATENT DOCUMENTS 1,793,861 A 2/1931 Ferdinand
1,880,088 A 9/1932 Guinzburg
(Continued)

FOREIGN PATENT DOCUMENTS

CN 203372610 1/2014
CN 204323753 5/2015
(Continued)

OTHER PUBLICATIONS

International Search Report, Application No. PCT/NZ2017/050026, dated Jun. 22, 2017, in 5 pages.

*Primary Examiner* — Chun Hoi Cheung
(74) *Attorney, Agent, or Firm* — Knobbe Martens Olson and Bear, LLP (57) ABSTRACT

Respiratory equipment packaging and insert for a respiratory interface assembly having a respiratory interface and headgear. The packaging includes a first pocket having a first opening, and being configured to enclose and sealing retain at least the respiratory interface and the headgear of the respiratory assembly, and a second pocket, adjacent the first pocket and having a second opening. The second pocket is configured to receive an auxiliary device intended for use with, or comprising part of, the respiratory interface assembly, such as a mask size measuring device. The insert is configured to support the respiratory interface in an upright orientation and includes at least one slot configured to receive a strap of the headgear of the respiratory interface assembly.

12 Claims, 11 Drawing Sheets

Related U.S. Application Data

(60) Provisional application No. 62/310,180, filed on Mar. 18, 2016.

(51) Int. Cl.
  B65D 30/22 (2006.01)
  B65D 33/25 (2006.01)

(52) U.S. Cl.
  CPC ..... B65D 33/2508 (2013.01); B65D 33/2541 (2013.01); A61M 2209/06 (2013.01)

(58) Field of Classification Search
  USPC ...... 206/286, 291, 292–298, 305, 39.7, 395, 206/419, 423, 525.1, 53, 702, 784, 805
  See application file for complete search history.

(56) References Cited

U.S. PATENT DOCUMENTS

| | | |
|---|---|---|
| 1,929,167 A * | 10/1933 | Goldsmith ............ G09F 5/042 206/231 |
| 2,632,564 A | 3/1953 | Bloom |
| 2,794,549 A * | 6/1957 | Feibusch ................ G09F 5/042 206/472 |
| 2,923,401 A | 2/1960 | Hagar |
| 4,248,363 A | 2/1981 | Zuckerman et al. |
| 4,629,101 A | 12/1986 | Franklin |
| 4,711,352 A | 12/1987 | Williams et al. |
| 5,699,909 A | 12/1997 | Foster |
| 5,988,373 A | 11/1999 | Yates |
| 6,003,672 A | 12/1999 | Chapman et al. |
| 6,345,716 B1 | 2/2002 | Chapman |
| 6,478,146 B1 | 11/2002 | Chapman |
| 6,691,868 B2 | 2/2004 | Roshdy |
| 7,028,838 B1 | 4/2006 | Rhoades |
| 7,743,920 B1 | 6/2010 | Lordo |
| 8,905,229 B1 | 12/2014 | Lane |
| 9,439,658 B2 | 9/2016 | Ford et al. |
| 2002/0014427 A1* | 2/2002 | van der Stoep ..... B65D 5/5035 47/84 |
| 2005/0051458 A1 | 3/2005 | Kopp et al. |
| 2006/0196788 A1 | 9/2006 | Komarnycky |
| 2016/0045701 A1 | 2/2016 | Arcilla et al. |

FOREIGN PATENT DOCUMENTS

| | | |
|---|---|---|
| GB | 2195898 | 4/1988 |
| WO | WO 2010/074557 | 7/2010 |

* cited by examiner

RESPIRATORY EQUIPMENT PACKAGING AND A PACKAGING INSERT FOR RESPIRATORY EQUIPMENT

INCORPORATION BY REFERENCE TO ANY PRIORITY APPLICATIONS

This application is a continuation of U.S. patent application Ser. No. 16/085,990, filed Sep. 17, 2018, which is a National Phase Application of PCT International Application No. PCT/NZ2017/050026, filed Mar. 17, 2017, which claims priority from U.S. Provisional Application No. 62/310,180 filed Mar. 18, 2016, the entire contents of all of these applications are hereby incorporated by reference herein and made a part of the present disclosure.

BACKGROUND

Field

This disclosure relates to respiratory equipment packaging for packaging a respiratory interface assembly comprising a respiratory interface and headgear mounted to the interface. In another aspect, the disclosure relates to a packaging insert on which a respiratory interface assembly can be retained for carrying, and/or to facilitate insertion into, and removal from, respiratory equipment packaging.

Description of Related Art

A respiratory interface assembly typically comprises a respiratory interface to which headgear is mounted, sometimes releasably. The headgear comprises one or more straps which connect to the interface and which extend over or around the head of the patient to retain the interface on the patient's head, with sufficient tension to ensure the interface is kept in the desired position and orientation, and to ensure an adequate seal, if a seal is required.

The respiratory interface may comprise any one of:
a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patients nares;
e) a nasal mask comprising one or more nasal pillows configured to seal against the patient's nose; and
f) a hybrid mask comprising a combination of nasal pillows/prongs and an oral seal.

The respiratory interface and headgear are typically supplied in a sealed packaging, such as a clear plastic packet or bag. It is important and often regulated that when used in a medical environment such as a hospital or the like, the parts of the respiratory interface that will come into contact with the patient's skin must be kept sealed in a clean and contaminant free condition until placed on the face of the patient. In particular, it is important that no exposed part of the healthcare provider, such as a nurse or other medical professional, touches the skin contacting parts of the respiratory interface. However, because of the practical difficulty in opening the sterile packaging, continuing to hold the packaging and simultaneously trying to remove the respiratory assembly from the packaging, it can often be the case that the medical professional accidentally touches a skin contacting part of the respiratory interface, destroying the cleanliness of that product and meaning that, in some instances, the respiratory interface assembly has to be discarded, or at least undergo extensive cleaning and/or sterilisation, if required. In some parts of a hospital, use and handling of a respiratory interface which is not, or may not be, contaminant free may be hazardous.

Likewise, it is often the case that the packaging includes some sizing device, such as a cardboard sizing guide, to determine which size of respiratory interface and headgear should be used with the patient in question, it typically being the case that there may be two or more sizes of interface and headgear. If a medical professional opens the sterile packaging, removes the sizing guide and then determines that a different size of interface and headgear is in fact required for the patient concerned, the interface and headgear is no longer sterile and must be discarded and another sterile packet opened for the correct size.

Not only is the above time consuming for the medical professional, it also results in a significant number of respiratory interfaces and headgear being thrown away, either because they are the wrong size, or because they are no longer considered sterile.

It is therefore an object of one or more embodiments of the disclosure to provide improved packaging and/or a packaging insert which overcome or at least ameliorate one or more disadvantages of the prior art, or alternatively at least provide the public with a useful choice.

Further objects of the disclosure will become apparent from the following description.

Accordingly in one aspect, an embodiment involves respiratory equipment packaging for packaging a respiratory interface assembly, the packaging comprising a first pocket having a first opening, and being configured to receive and sealingly enclose the respiratory interface assembly such that the respiratory interface assembly can be sealed in the first pocket in a clean condition, the packaging further comprising a second pocket, adjacent the first pocket and having a second opening, the second pocket being configured to receive an auxiliary device intended for use with, or comprising part of, the respiratory interface assembly. Each opening comprises a respective closure configured to close each opening.

In some configurations, the first pocket may be dimensioned to receive and sealingly enclose a respiratory interface assembly comprising at least a respiratory interface and headgear. The first pocket may be larger than the second pocket in terms of at least one of: height, width, depth and volume. Each pocket may be opened and closed independently of the other. That is, one pocket can be opened whilst the other pocket remains closed.

In some configurations, each closure may comprise a seal configured to enable the contents of each pocket to be sealed therein in a clean condition. The seal, or each seal, may be reusable. At least one closure may comprise a reusable closure configured such that at least one pocket can be repeatedly opened and closed. One or more of the openings may be provided with a pull tab configured to be pulled to open the associated pocket.

In some configurations, the packaging may further comprise at least one region of predetermined weakness configured such that one part of the packaging may be removed from another part of the packaging by separation at the region of predetermined weakness. The at least one region of predetermined weakness may be provided between the two pockets such that one pocket may be separated from the other pocket by separation at the region of predetermined weakness. The at least one region, or another region, of predetermined weakness may be provided at the second pocket such that the second pocket may be opened by separation of part of the packaging at the region of predetermined weakness. A plurality of regions of predetermined weakness may be provided to enable different parts of the packaging to be separated.

In some configurations, at least one additional pocket may be provided.

In some configurations, the packaging may be formed of a plastic material and my be formed from a single sheet of material. In some examples the material is a flexible material. In some examples, the packaging comprises a bag of a flexible material.

In some configurations, the packaging is configured such that the first pocket is dimensioned to receive headgear and a respiratory interface selected from the group comprising:
a) a full face mask comprising a mask frame and a cushion configured to seal around the patient's nose and mouth;
b) a nasal mask comprising a mask frame and a cushion configured to seal around the patient's nose; and
c) a nasal cannula having one or more prongs for insertion into the patient's nares.
d) The packaging is preferably configured such that the second pocket is dimensioned to receive an auxiliary device selected from the group comprising:
e) operating instructions for operating the respiratory interface assembly; and
f) a planar mask size measuring guide.

In another aspect, an embodiment involves a packaged respiratory interface assembly comprising packaging as described in any of the preceding paragraphs of this section, and further comprising a respiratory interface and headgear sealingly enclosed in the first pocket, and an auxiliary device contained in the second pocket.

In a further aspect, an embodiment involves a packaging insert configured to retain a respiratory interface assembly prior to inserting the insert and respiratory interface assembly into suitable packaging, the insert comprising an elongate support having a notional longitudinal axis, an upper part, a lower part, and opposed, spaced apart sides extending between the upper and lower parts, the support further comprising a headgear retaining slot formed in or at each side, each slot being elongate and comprising a width that is dimensioned to receive and retain part of a strap of the headgear, each slot further comprising a closed end and an open end, and being configured such that when, in use, the insert is picked up by one hand of a user with the upper part of the insert uppermost, each slot is downwardly directed such that the open end is open towards the lower part of the insert such that the user can use their other hand to grip the respiratory interface and pull downwardly to release the headgear from the slots.

According to another aspect, an embodiment involves a packaging insert configured to retain a respiratory interface assembly, the insert comprising:
an elongate support having a notional longitudinal axis, an upper part, a lower part, and opposed, spaced apart sides extending between the upper and lower parts, the support further comprising a headgear retaining slot formed in or at each side, each slot being elongate, each slot further comprising a closed end and an open end, wherein each slot is downwardly directed such that the open end is open towards the lower part of the insert.

In some configurations, the support further comprises at least one retaining arm depending from at least one side, at least one slot being defined between the retaining arm and the side of the support.

In some configurations, the insert may comprise four retaining arms and four slots, there being an upper and a lower retaining arm and an upper and lower slot on each side of the support.

In some configurations, at least one arm or side may comprise an inwardly directed retaining portion, adjacent the open end of the slot, and which defines a reduced width portion of the slot adjacent the retaining portion, the reduced width portion being configured to help retain a strap of the headgear in the slot. The other of each arm or side of the support may comprise an indented portion adjacent the inwardly directed retaining portion, and configured, with the retaining portion, to define a circuitous path into the slot.

In some configurations, at least one slot comprises an inclined portion, adjacent the open end of the slot, the inclined portion defining a widening mouth of the slot configured to facilitate insertion of a strap of the headgear into the slot, the widening mouth leading to a narrower elongate portion in which the strap of the headgear is retained.

Each slot has a respective longitudinal axis, and in some examples the longitudinal axis of at least one slot is parallel with the longitudinal axis of the support. The longitudinal axis of each slot may be parallel with the longitudinal axis of the support. In other examples, the longitudinal axis of at least one slot may be inclined with respect to the longitudinal axis of the support. The longitudinal axis of each slot may be inclined with respect to the longitudinal axis of the support.

In some configurations, the insert further comprises a carry handle at or adjacent the upper part of the support.

In some configurations, the support is generally oblong, and may comprise a wider upper part and a narrower lower part. At least part of the sides of the support may be substantially straight and parallel. At least part of the sides of the support may be arcuate.

In some configurations, the lower part of the support preferably comprises a foot of the support. This can assist in keeping the support upright during transit and/or storage.

Accordingly in one aspect, an embodiment involves respiratory equipment packaging for packaging a respiratory interface assembly retained on a packaging insert of any of the above statements of invention.

According to a further aspect, an embodiment involves a packaged respiratory interface assembly comprising packaging as described in any of the preceding paragraphs of this section, and further comprising an insert as described in any of the preceding paragraphs of this section, a respiratory interface and headgear mounted on the insert and sealingly enclosed in the first pocket, the assembly further comprising an auxiliary device contained in the second pocket.

Further aspects of the invention, which should be considered in all its novel aspects, will become apparent from the following description.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although the disclosure describes examples and reference to possible embodiments, it is to be understood that modifications or improvements may be made thereto without departing from the scope of the disclosure. Embodiments of the invention may also be said broadly to consist in the parts, elements and features referred to or indicated in the specification of the application, individually or collectively, in any or all combinations of two or more of said parts, elements or features. Furthermore, where reference has been made to specific components or integers of the disclosed embodiments having known equivalents, then such equivalents are herein incorporated as if individually set forth.

Any discussion of the prior art throughout the specification should in no way be considered as an admission that such prior art is widely known or forms part of common general knowledge in the field.

BRIEF DESCRIPTION OF THE DRAWINGS

A number of embodiments of the disclosure will now be described by way of example with reference to the drawings in which.

DETAILED DESCRIPTION

Throughout the description like reference numerals will be used to refer to like features in different embodiments.

Referring to FIGS. 1 to 4, there is provided respiratory equipment packaging 1 for packaging a respiratory interface assembly 3 comprising at least a respiratory interface 5 and headgear 7 for mounting the respiratory interface 5 on the face of a patient. The packaging 1 comprises a first pocket 11 having a first opening 13, and being configured to enclose and sealing retain at least the respiratory interface 5 and the headgear 7 of the respiratory assembly, and a second pocket 15, adjacent the first pocket 11 and having a second opening 17. The first pocket 11 is relatively large as compared to the second pocket 15. The second pocket 15 is configured to receive an auxiliary device 19 intended for use with, or comprising part of, the respiratory interface assembly 3.

Figure 5:
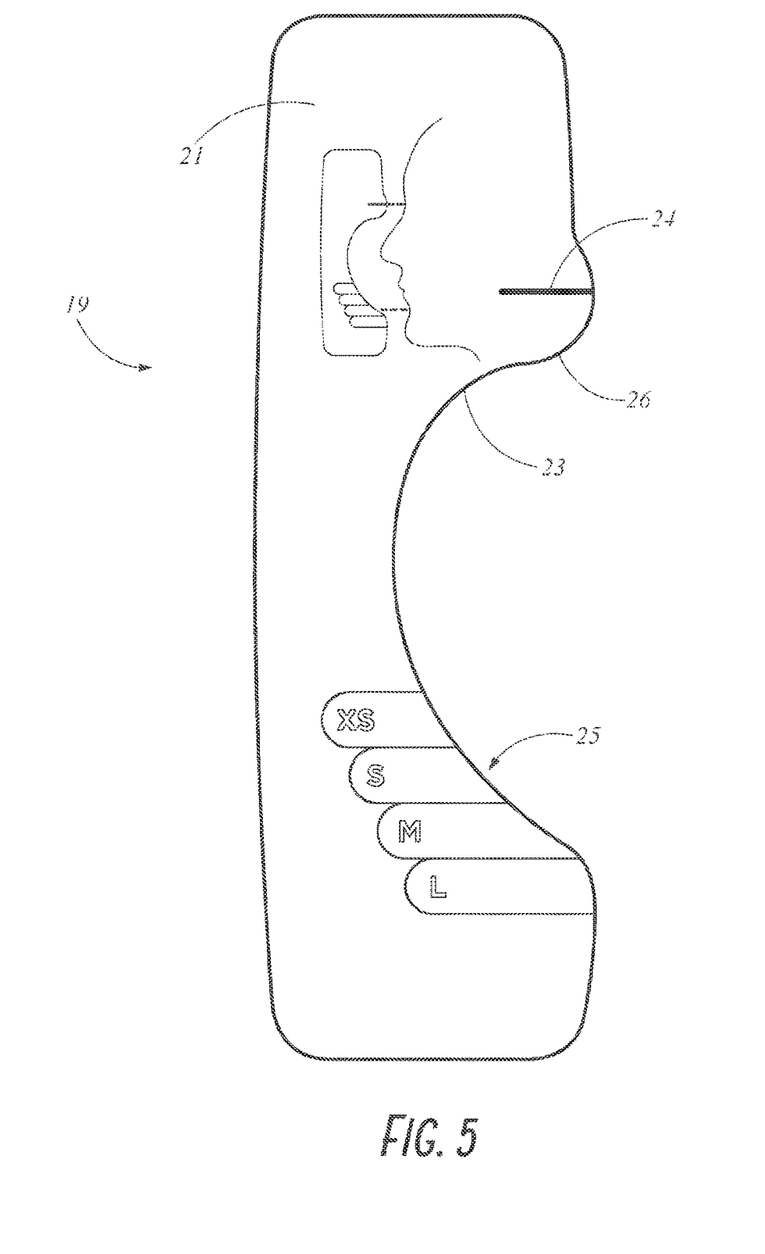
FIG. 5 is a front view of auxiliary device comprising a size guide which can be included in packaging in accordance with embodiments disclosed herein.
Figure 6:
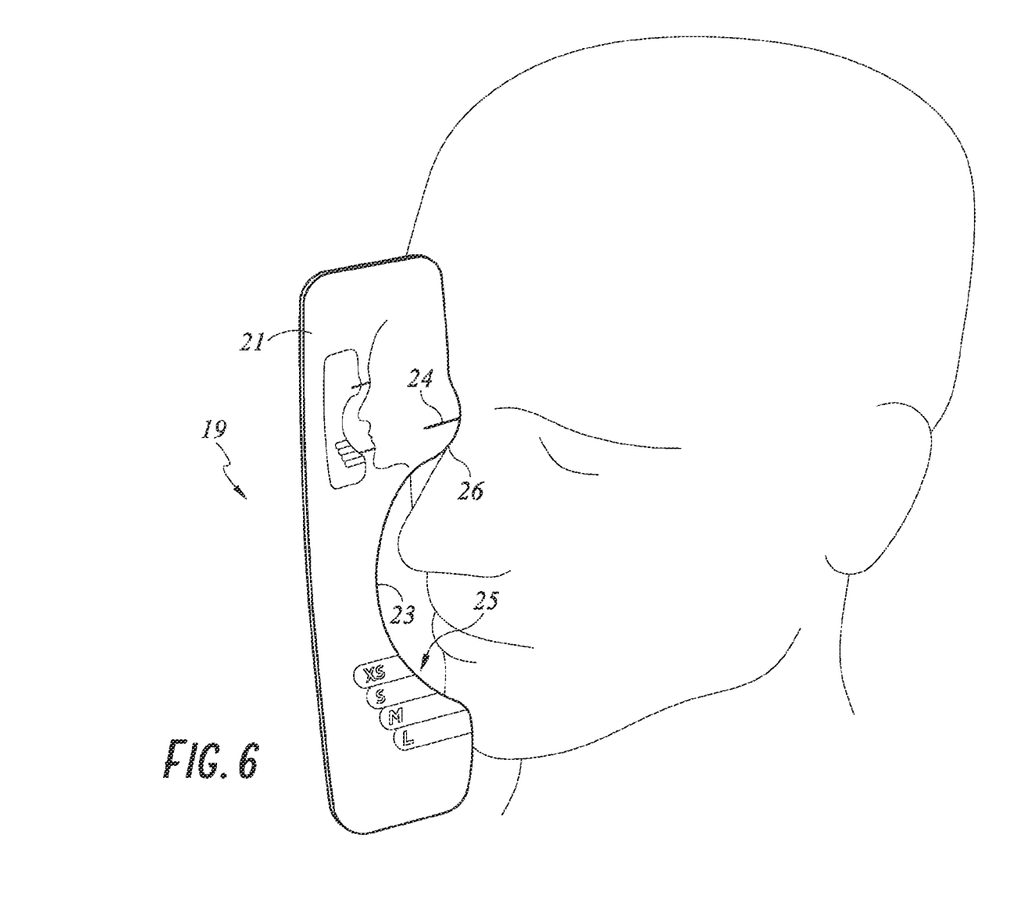
FIG. 6 is a perspective view of the size guide of FIG. 5 in use.

With additional reference to FIGS. 5 and 6, in this example, the auxiliary device 19 comprises a planar mask size measuring guide configured to be placed against the face of the patient to determine the size of patient interface appropriate for the patient concerned. The measuring guide 19 comprises a planar body 21, one side margin 23 of which is profiled to broadly match the shape, in profile, of the nasal-oral region of a patient's face. The guide 19 comprises indicia 25 which indicate to the user which size of respiratory assembly should be used, when an eye alignment mark or line 24 is vertically aligned with the patient's eye line. This mark or line 24 is a reference point or reference line that is aligned with the nasion intersection of a patient's face, that is, the location on the nasal bridge in between the eyes. This mark or line 24 acts as a reference point that is aligned first, the size of respiratory assembly 3 being determined by placing the reference line 24 on the nasion intersection. This occurs when the upper rounded protruding part 26 of the body 21 is resting on the nasal bridge of the patient, and identifies the center of the eye of the patient. This provides a reference point for all other measurements regarding the size of patient interface required for the patient concerned.

Figure 1:
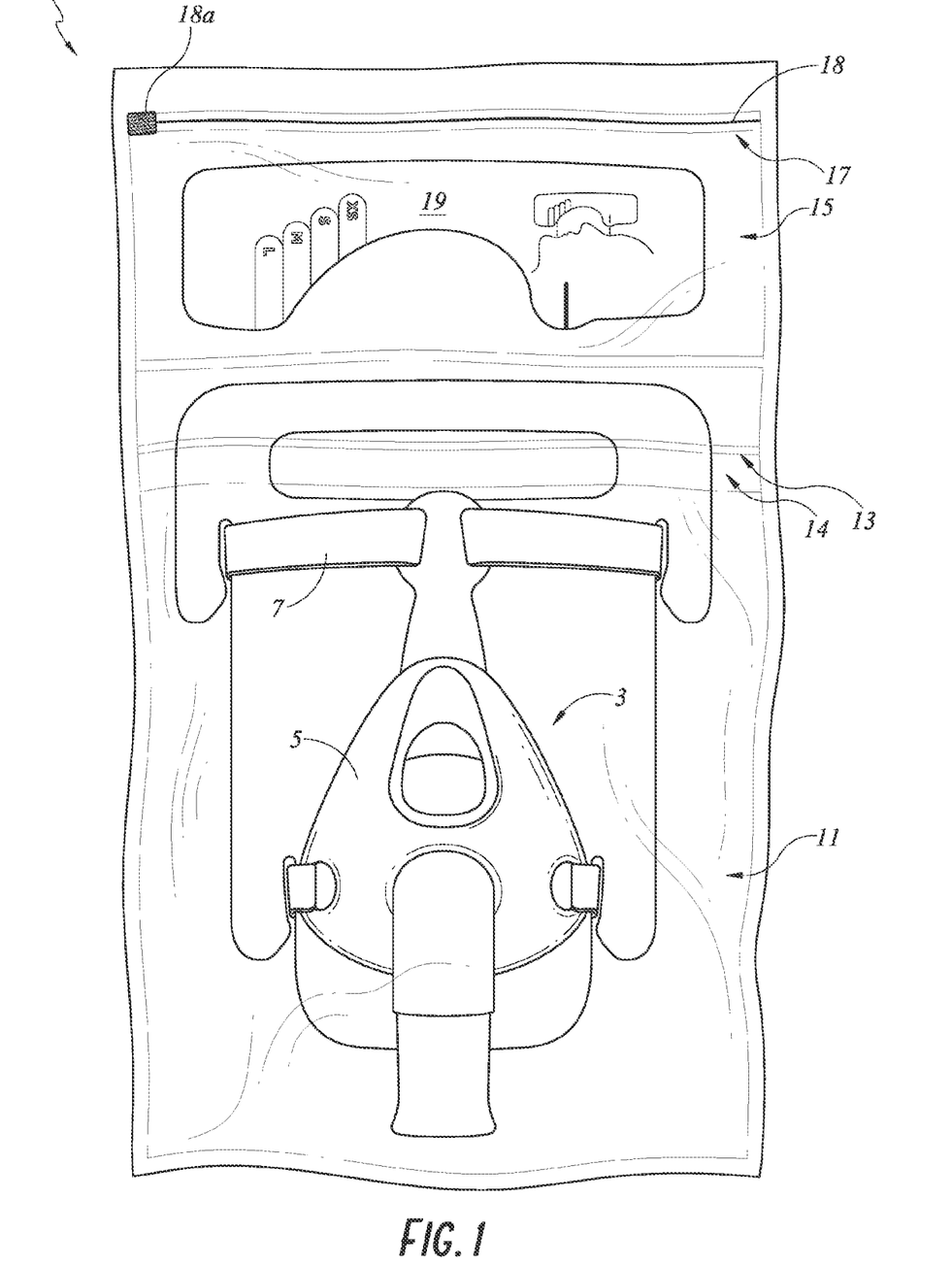
FIG. 1 is a front view of a first embodiment of respiratory equipment packaging.
Figure 2:
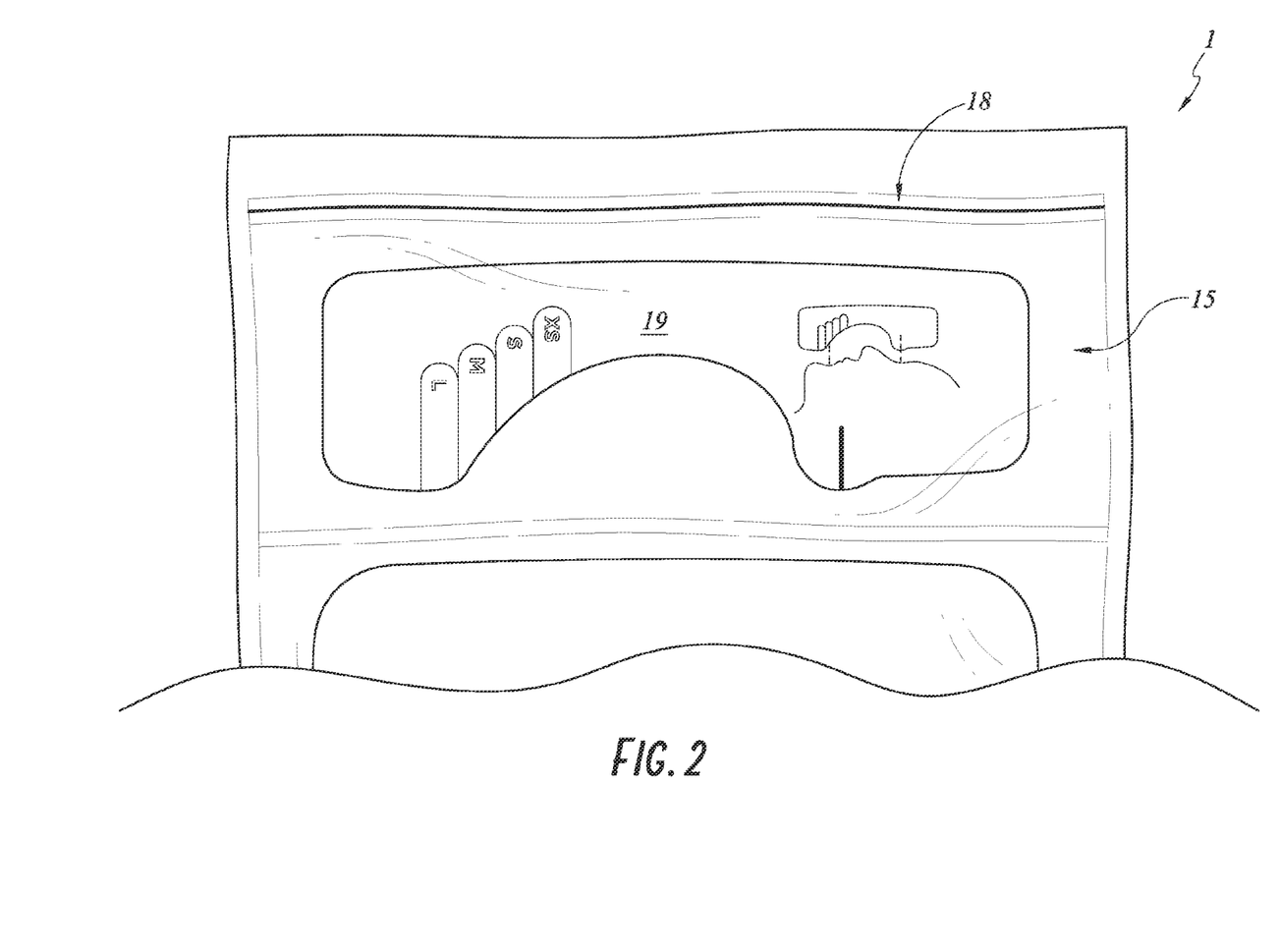
FIG. 2 is an enlarged view of a top part of the packaging of FIG. 1.
Figure 3:
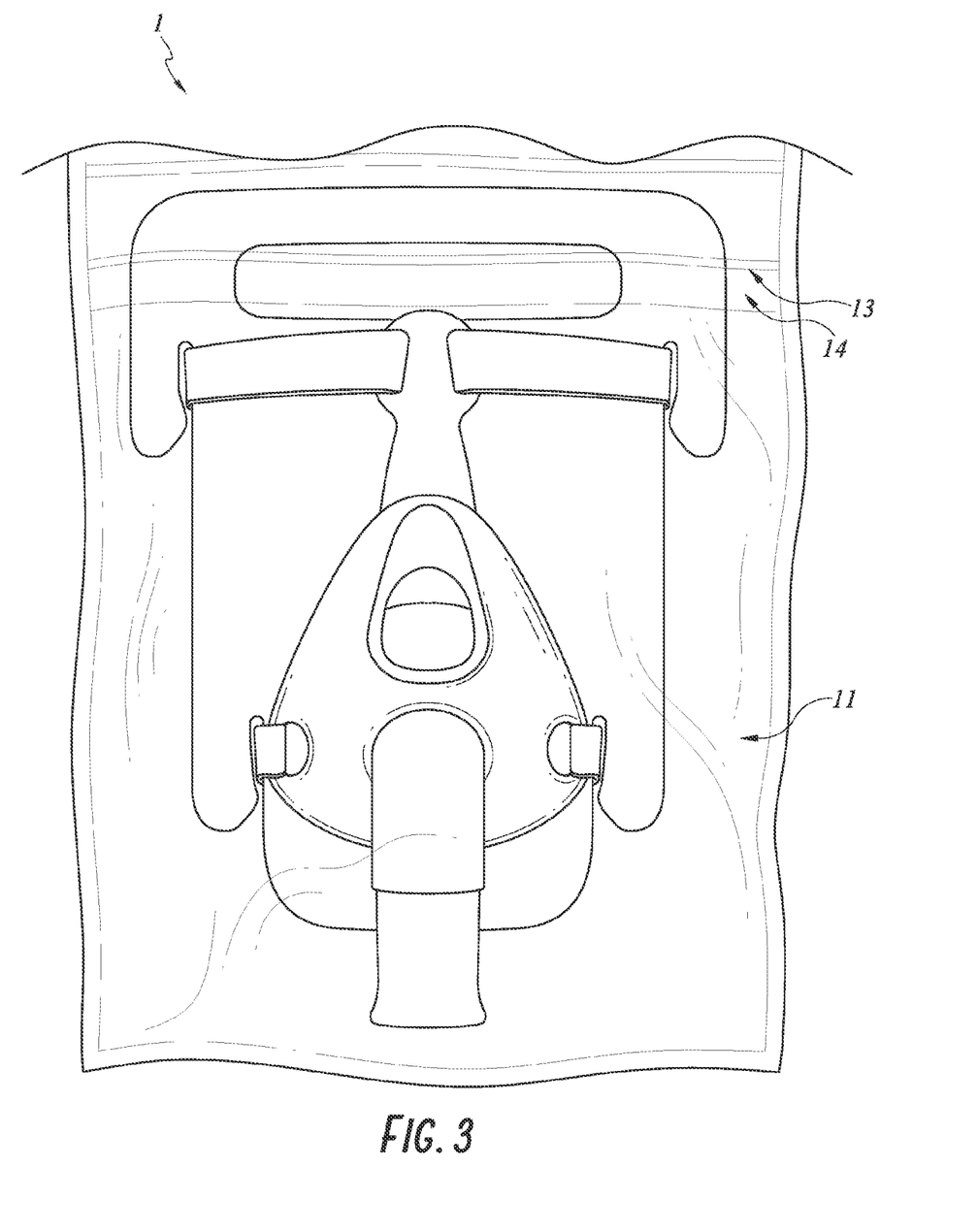
FIG. 3 is an enlarged view of a lower part of the packaging of FIGS. 1 and 2.

The packaging 1 in this example is generally oblong with oblong pockets 11, 15. The pockets 11, 15 are the same width, but different heights, lower pocket 11 being larger in this example than the upper pocket 15. The pockets 11, 15 may differ in size in terms of height and/or width and/or depth, and/or volume. The packaging 1 in this example comprises a bag formed from a flexible material which in this example is an airtight, transparent plastics material. The openings 13 and 17 are elongate and each extend across the width of the packaging. The pockets 11, 15 could be any other desired shape, and one or more of the pockets 11, 15 may for example be square, the shape and size being selected to correspond to the type and/or size and/or shape of the particular respiratory assembly 3 with which the packaging 1 is used.

Each opening 13, 17 is provided with a closure 14, 18. In this example, the closure 14 of the opening 13 comprises a single use sealing strip which seals the larger pocket 11 closed and which can be torn open to access the larger pocket 11. In this example, the closure 18 of the opening 17 comprises a repeated use sealing closure of the type comprising two spaced apart lips which can be releasably sealed together using a slider 18a which can be slid along the lips from one side of the packaging to the other to force the two lips together. Each opening 13, 17 may be provided with any suitable type of closure. Each closure may be single use or repeated use. One or both closures may be a sealing closure configured to seal the respective pocket when closed, and one or both closures may be a resealable closure. Other examples of closures that might be used include zips, poppers, hook and loop type fasteners, and/or buttons on one part of the opening that are received in corresponding button holes on another part of the opening.

Figure 4:
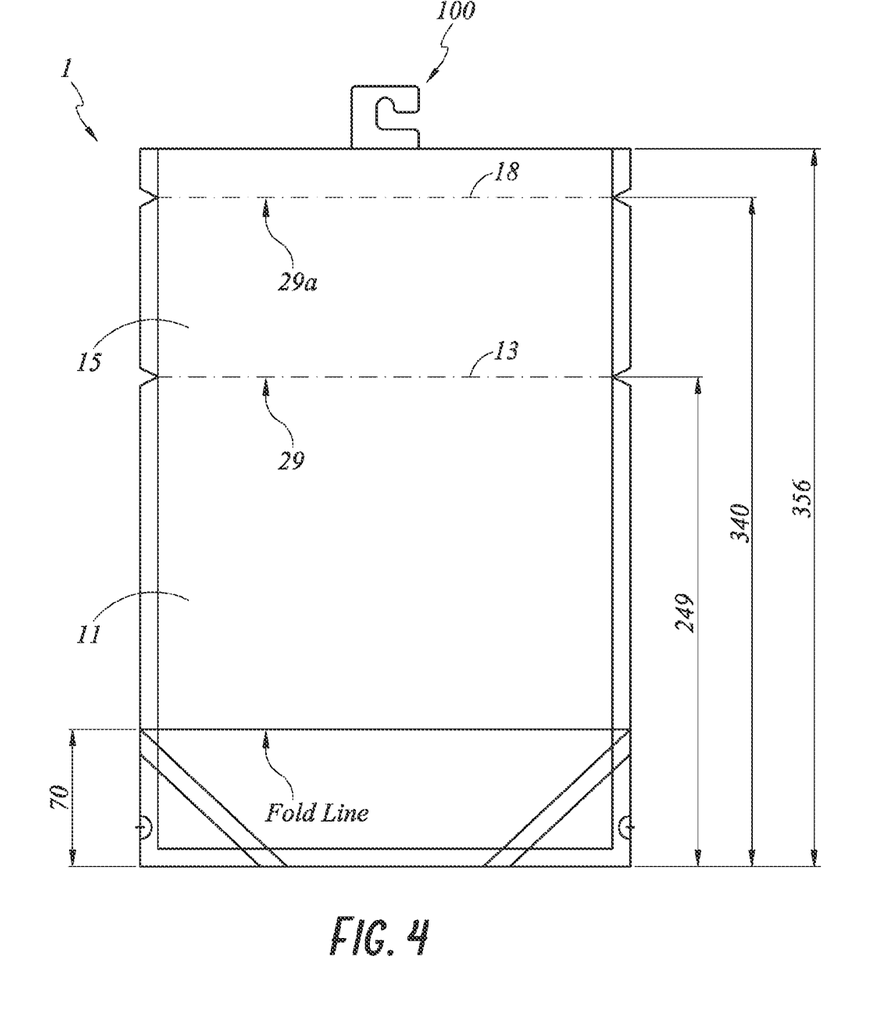
FIG. 4 is a plan view of a blank used to form the packaging of FIGS. 1 to 3.

With reference to FIG. 4, the packaging 1 may be formed from a single blank of material which is folded and the seams secured together using any suitable technique which may include hot or cold adhesive or hot plate welding, for example.

The larger and smaller pockets 11, 15 may be releasably secured together so that one pocket 11, 15 can be removed from the other. For example, a first region of predetermined weakness, such as a perforated tear line 29, may be provided between the two pockets 11, 15 so that one pocket 11 can be torn from the other pocket 15. In one example, the larger and smaller pockets 11, 15 may be separable, for example by being torn apart along a line of predetermined weakness, with the opening of each pocket 11, 15 being provided with a resealable closure (such as the closures 14 and 18 of FIGS. 1-3). Thus, each pocket 11, 15 can be opened and resealed repeatedly, and independently of the other, even when the pocket 11 has been separated from the pocket 15.

A second region of predetermined weakness, such as perforated tear line 29A, may be provided at the top of upper, smaller pocket 15. The dual pocket packaging 1 thus includes a pair of tear off zones. The upper tear line 29A can be used to open the upper pocket 15 to access the measuring guide 19 while maintaining the lower, larger pocket 11 containing the respiratory assembly 3 in a sealed configuration. The second or lower tear line 29 can be used to open the respiratory assembly pocket 11 to access the respiratory assembly 3 while maintaining the measuring guide pocket 15 in a sealed configuration.

It is intended that the upper smaller pocket 15 contains equipment auxiliary to the respiratory interface assembly 3, and which might be used prior to needing to decide on which size of respiratory interface is required, and therefore prior to opening the larger pocket 11. In this example, the sizing guide 19 can be removed from the upper pocket 15 and used to determine the size of interface required. If an interface is required which is different from the size contained in the lower pocket 11, the lower pocket 11 can remain sealed closed and another packaging assembly selected containing the correct size of interface. Thus, a medical professional need not throw away an entire patient interface assembly when they determine that a different size is required, as only the upper pocket 15 need be opened to make that determination.

The packaging 1 may include a slot or hook 100 or other device configured to enable the packaging 1 to be hung in a storage location, for example near a patient bedside, or in a storage location.

One or more of the openings 13, 17 may be provided with a pull tab, loop or hand grip region configured to be gripped and pulled to open the associated pocket 11, 15.

Referring now to FIGS. 7 to 11, a packaging insert 31 is provided on which the respiratory interface assembly 3 may be mounted and retained prior to inserting the insert 31 and respiratory interface assembly 3 into suitable packaging 1, as described above with reference to FIGS. 1 to 4.

Figure 7:
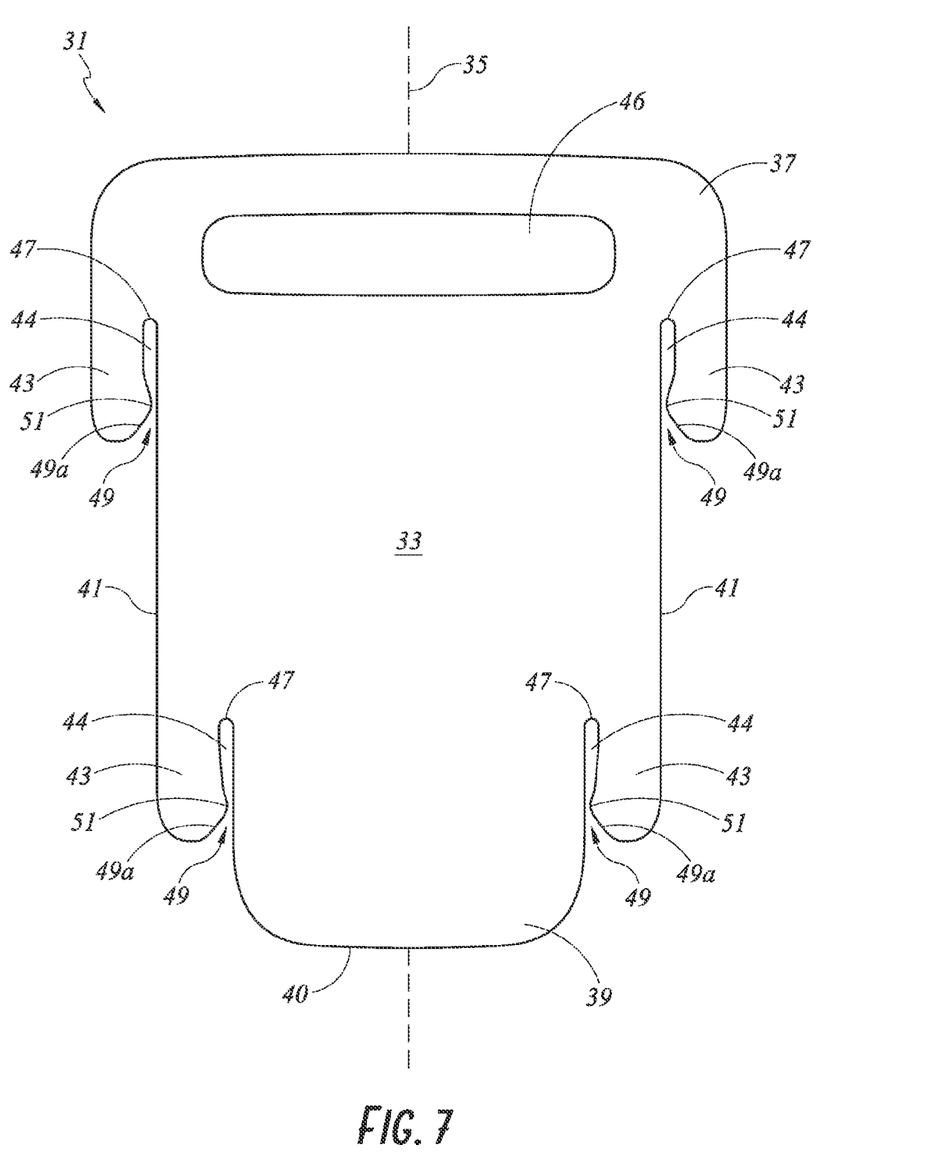
FIG. 7 is a plan view of a first embodiment of a packaging insert.

The insert 31 comprises a substantially planar elongate support 33 having a notional longitudinal axis 35, an upper part 37, a lower part 39, and opposed, spaced apart sides 41 extending between the upper and lower parts 37, 39. At least one pair of retaining arms 43 depends from each side 41. The lower part 39 comprises a straight region which functions as a foot 40. The foot 40 extends below the lowest part of the respiratory interface assembly 3 when mounted on the insert 31. The foot 40 is shaped to support the insert 31 in an upright position during transport and during storage. The stability provided by the foot 40 ensures the respiratory interface assembly 3 and insert 31 are protected to some degree during transport and storage. The flat shape of the foot 40 allows the insert 31 to be stood up vertically. This is advantageous because the respiratory interface assembly 3 is presented to the nurse in an in-use state, that is, with the respiratory interface assembly 3 in the orientation in which the assembly 3 would be used. This provides the nurse with a visual cue as to the visual orientation of the respiratory interface assembly 3 so that the nurse receives a visual indication of how the respiratory interface assembly 3 should look, when used on a patient. The respiratory interface assembly 3 is therefore presented and stored in an in-use state on the insert 31 to provide a visual guide to the nurse.

The insert 31 may be made front a cardboard material, or a plastics material for example. The insert 31 may be configured to be disposable.

Figure 11:
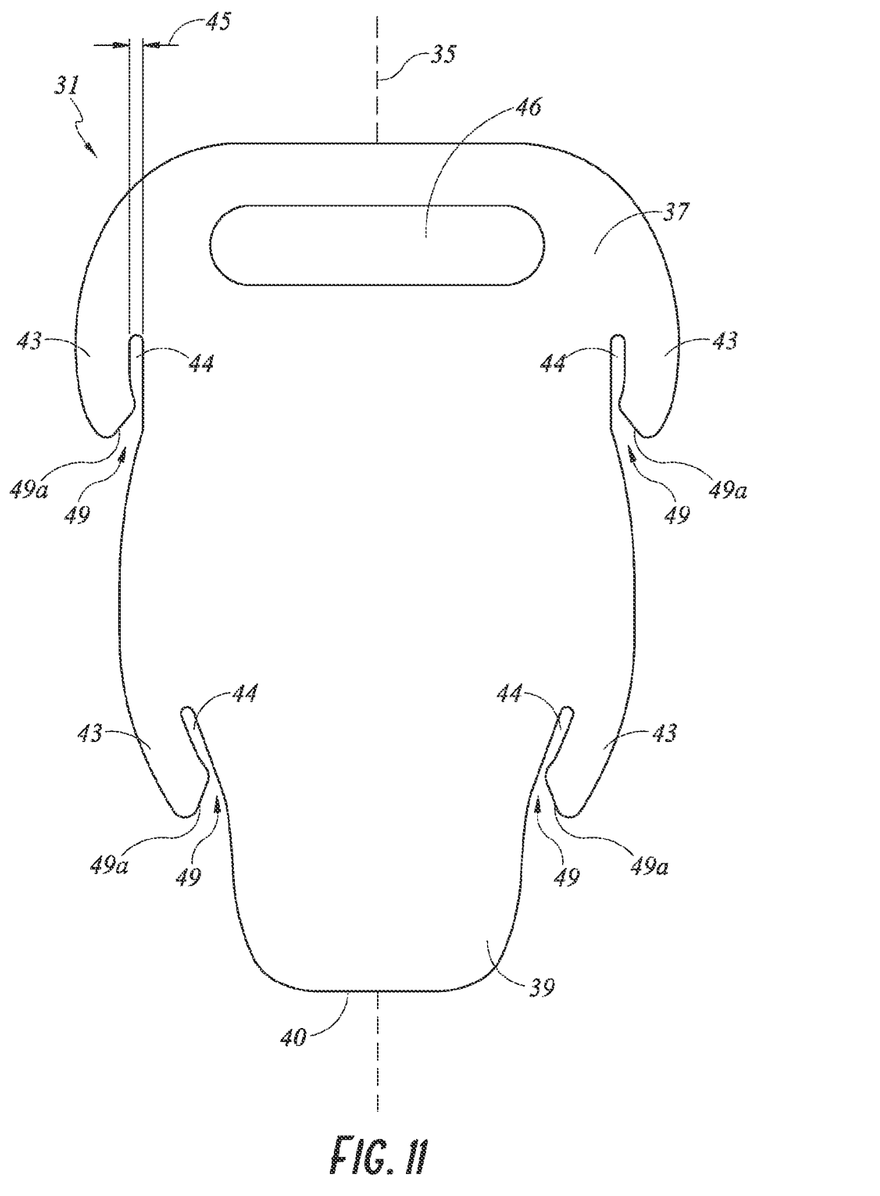
FIG. 11 is a plan view of yet another embodiment of a packaging insert.

A headgear retaining slot 44 is defined between each retaining arm 43 and the respective side 41, each slot 44 being elongate and having a width 45, see FIG. 11, between the respect retaining arm 43 and side 41 dimensioned to receive and retain a strap 7A of the headgear 7. Each slot 44 further comprises a closed end 47 and an opening or mouth 49. The mouth 49 is open towards the lower part 39 of the insert 31 such that when the insert 31 is picked up by one hand of a user with the upper part 37 of the insert uppermost, the user can use their other hand to grip the respiratory interface 5 and pull downwardly to release the headgear 7 from the slots 44. A carrying handle 46 may be provided to assist one handed handling of the insert 31.

Figure 8:
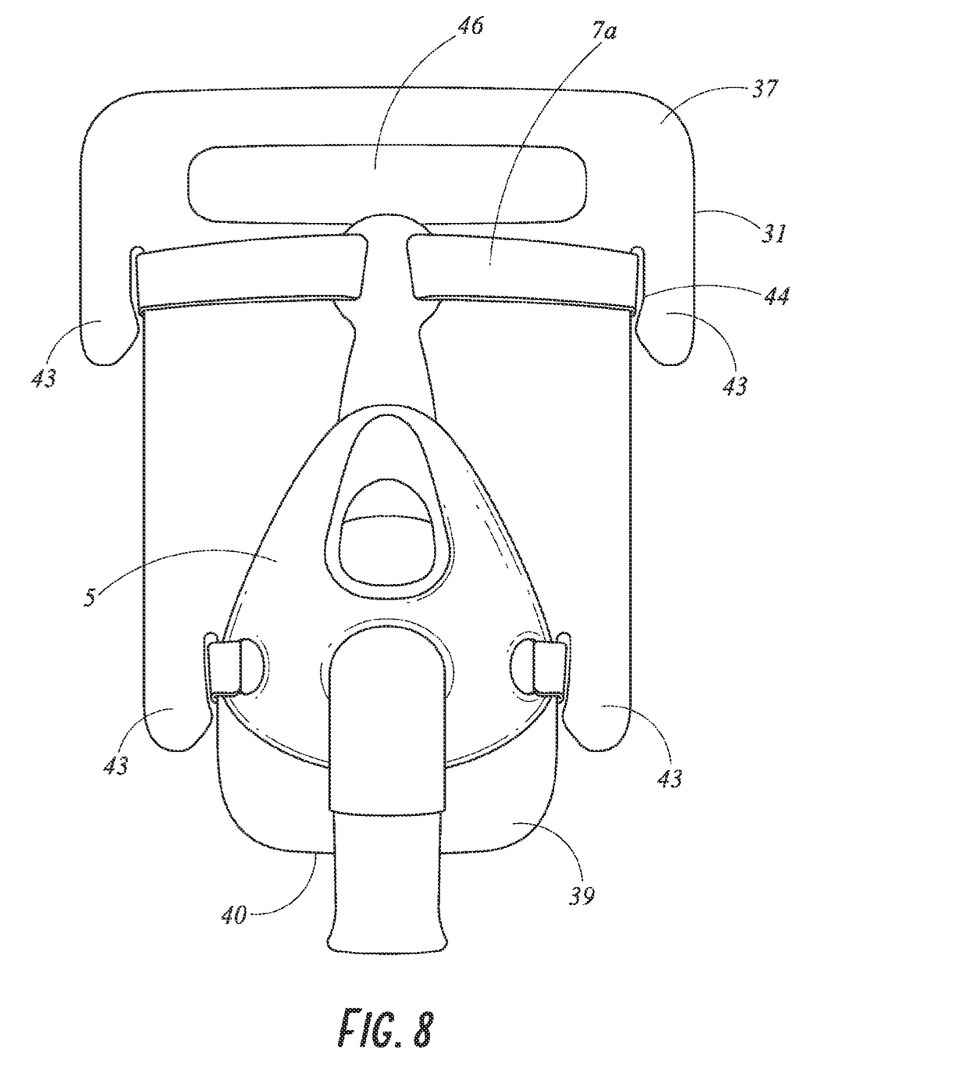
FIG. 8 is a plan view of the packaging insert of FIG. 7 on which a respiratory interface assembly is mounted.

With additional reference to FIG. 8, this configuration, with every slot 44 being generally downwardly directed with the opening or mouth 49 of the slot 44 being lowermost, ensures that a user only has to grip the respiratory interface assembly with one hand, with the other hand holding the insert 31. Provided the user grips a non-face contacting portion of the interface 3, there is no possibility of the user inadvertently touching a face contacting portion of the interface 3 with the resulting undesirable loss of sterility. There is also no need for the user to grip the headgear 7 itself, which again minimizes any possibility of inadvertently touching the face contacting parts of the interface 3. The insert 31 may comprise a handle 46 at the upper end 37 to further facilitate single handed holding of the insert 31.

The width of each slot 44, in a direction generally perpendicular to the longitudinal axis 35 between each side 41 of the support and each arm 43, can be selected to ensure a suitable retaining force is exerted on the headgear straps 7A whilst also enabling the strap 7A to be inserted into, and subsequently pulled from, each slot 44 when required. This dimension may be determined with reference to the ratio of the width of the strap 7A to the width of the slot 44 for example.

One or more slots 44 may be provided with additional retaining features configured to help retain each headgear strap 7A in the respective slot 44.

With reference to FIG. 7, each slot 44 comprises an inwardly directed retaining portion 51 adjacent the opening 49 of the slot and projecting radially into the slot 44 to reduce the width of the slot 44 adjacent the slot opening or mouth 49. The retaining portion 51, because of the narrower width of the slot 44 in that region, exerts an additional retaining force on the headgear strap 7A to help retain the headgear on the insert 31. In this embodiment, the insert 31 is generally oblong and comprises a wider upper part 37 and a narrower lower part 39. Each slot 44 has a longitudinal axis and in this example these axes are parallel to the longitudinal axis 35 of the insert 31. Each slot 44 comprises a pair of parallel walls.

Each opening 49 is defined in part by an inclined region 49A of the slot 44, the region 49A being inclined relative to the longitudinal axis 35 of the insert 31 preferably between 30 and 55 degrees, and in one embodiment by about 45 degrees. The inclined region 49A and opening 49 function as a lead-in to the slot 44, by a defining a widened mouth to simplify and facilitate inserting straps 7A into the slots 44.

Figure 9:
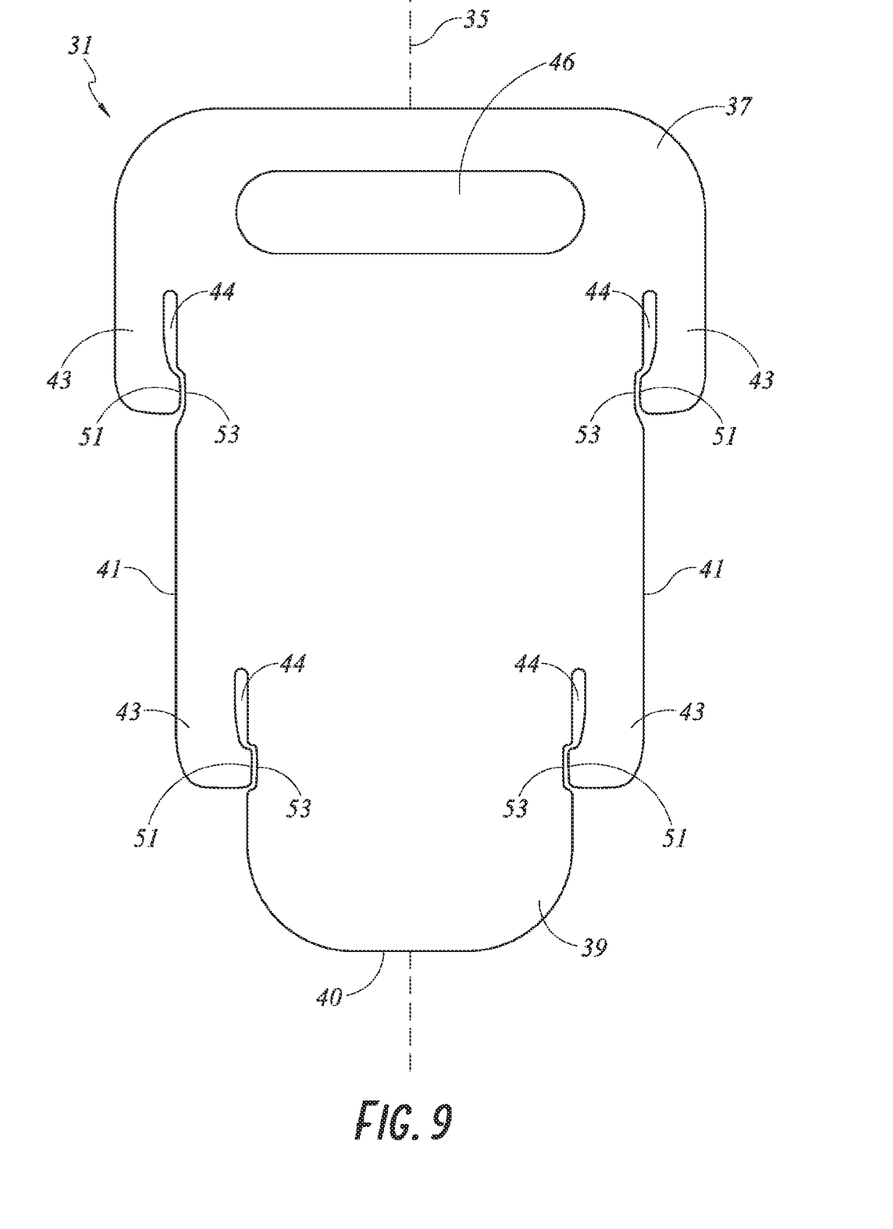
FIG. 9 is a plan view of a further embodiment of a packaging insert.

With reference to FIG. 9, the retaining portion 51 may be positioned adjacent a corresponding indent 53 formed in the sides 41. The retaining portion 51 and indent 53 comprise a region of narrowed width forming a circuitous path for the headgear strap 7A at the mouth opening 49 of each slot 44. This circuitous path may help to retain the strap 7A in each slot 44. In this example, the elongate part of each slot 44 comprises an arcuate wall and an opposed straight wall, being the straight side 41 of the insert 31. The slots 44 in this example therefore have non-parallel walls.

Figure 10:
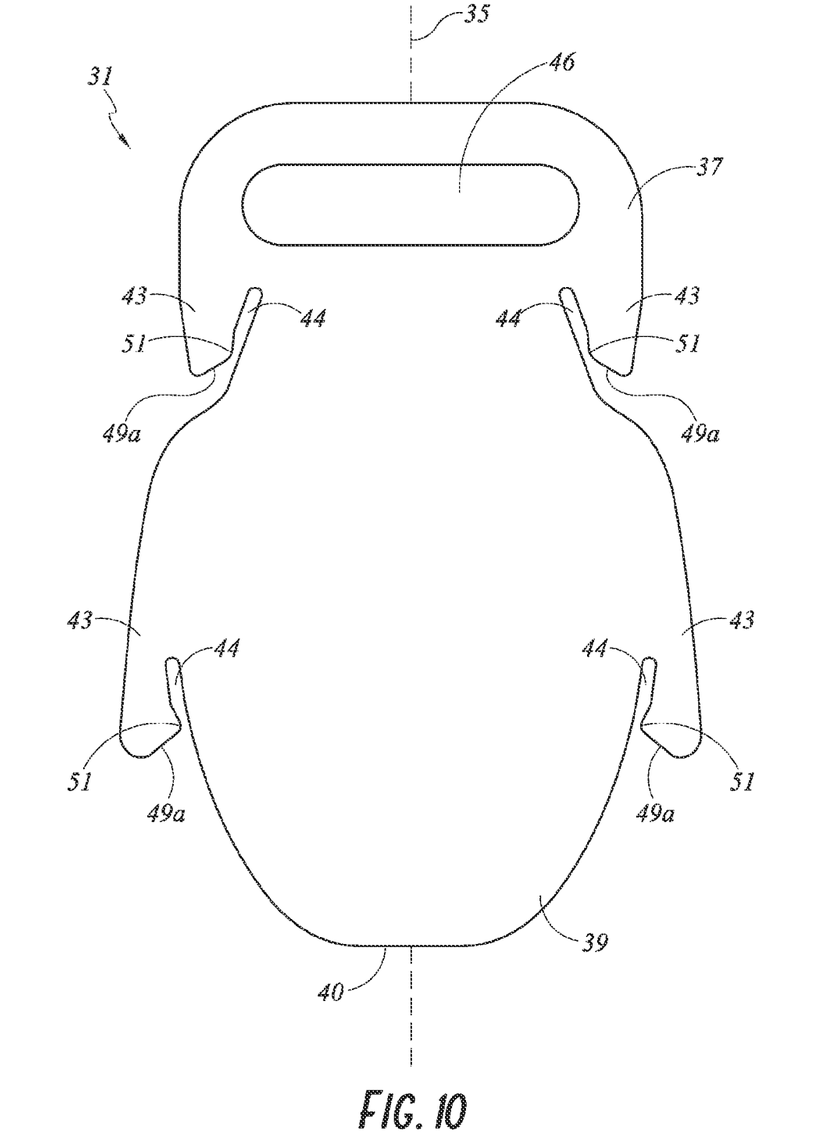
FIG. 10 is a plan view of another embodiment of a packaging insert.

With reference to FIG. 10, in this example the longitudinal axis of each slot 44 is inclined relative to the longitudinal axis 35 of the insert 31. The upper pair of slots 44 are inclined outwardly, whereas the lower pair of slots 44 are inclined inwardly. In this example the upper and lower parts 37, 39 of the support 33 are of similar width, with an intermediate region of the insert 31 being of greater width. The lower part 39 in this example comprises arcuate sides which are into a substantially straight support base region such that the foot 40 has a straight bottom surface. The slots 44 in this example have generally parallel but arcuate walls. In this example, the opening or mouth 49 of each slot 44 comprises an inclined region 49A such that the mouth 49 is relatively wide to facilitate insertion of the headgear strap 7A into the slots 44.

With reference to FIG. 11, a further embodiment of the insert 31 comprises a pair of upper slots 44 whose longitudinal axes are generally parallel to the longitudinal axis 35 of the insert 31, and a pair of lower slots 44 whose longitudinal axes are inwardly inclined relative to the longitudinal axis 35 of the insert 31. In this example, the opening or mouth 49 of each slot 44 comprises an inclined region 49A as with the example of FIG. 10 above. FIG. 11 shows an insert 31 having dimensions which may provide a good balance between retaining the headgear 7 on the insert 31 as the insert 31 is removed from the packaging 1, and also allowing the headgear 7 to be relatively easily removed from the insert with one hand as described above.

The ratio of the width of each slot 44 as compared to width of the headgear strap 7A may be between 0.1 and 1.0, preferably 0.2-0.9 and, in one embodiment, is between 0.4-0.7. Thus, in a preferred embodiment, the width of each slot 44 is smaller than the width of the headgear straps 7A. Alternatively, the straps of the headgear may be between 1.2 to 3 times wider than the slot width, preferably 1.3 to 2.8, and in one embodiment are between 1.5 to 2.5 times wider than the slot width. Each slot 44 is preferably narrower than the headgear strap width in order to compress the strap to hold the strap 7A within the slot 44 via a friction fit. However, the width of each slot 44 is such that it still allows for relatively easy removal of the strap 7A from the slot 44. The width ratio is such that the straps 7A are gripped within the slots 44 such that the straps 7A resist falling out of the slots 44 during transportation for example. In some configurations, the slots 44 may each have a width of between about 3-6 mm, 4-5 mm or about 4.5 mm. The insert 31 can have an overall height of between about 250-275 mm, or about 265 mm (e.g., 262 mm) and a width at an intermediate section between the upper and lower slots 44 of between about 150-170 mm, or about 160 mm (e.g., 159 mm). A depth of the mouth 49 of the slot 44 can be about 10-20 mm, about 15-17 mm, or about 16 mm (e.g., 15.88 mm). The depth and spacing of the slots 44 can be related to the height of the headgear straps 7A and the spacing of the headgear straps 7A on the interface 5.

The height of the handle aperture 46 at the top of the insert 31 (i.e. the handle that is gripped by the nurse to pull out the insert 31) is preferably between 20 mm and 40 mm. The lower end of the range is selected so that the nurse's fingers can be comfortably inserted and curled around the handle 46 to grip the handle 46. The upper end of the range is to ensure that the overall height of the insert 31 is minimized to reduce the amount of material used for the insert 31. The handle 46 extends above the upper portion of the mask that is retained on the insert 31, so that the nurse can grasp the handle 46 without contacting the mask. The handle 46 is also configured so that the nurse can remove the insert 31 one handed. These dimensions are not limiting and other dimensions and dimension combinations are within the scope of the invention.

The overall size and shape of the insert 31 may be chosen so as to minimize the amount of material needed to create the insert 31. If the insert 31 is stamped or cut from a larger sheet of material, the shape of the insert 31 may be designed to minimize the amount of material wasted between adjacent inserts 31 on the sheet.

With the examples of FIGS. 7 to 11, each insert 31 comprises an upper pair of slots 44 and a lower pair of slots 44. However, in other embodiments only a single pair of slots 44 may be provided. This would be appropriate in the case of a typically smaller respiratory assembly 3 having headgear having only one strap rather than a pair of straps. For example, a respiratory assembly comprising a patient interface in the form of a nasal cannula, nasal pillows, or other type of nasal mask, might have headgear which only has one strap, rather than the upper and lower straps that might be provided on a full-face mask for example.

In a yet further example, the sides 41 of the insert 31 may comprise an inwardly directed retaining portion adjacent the opening 49 of each slot 44 and projecting radially into the slot 44 to reduce the width of the slot 44 adjacent the slot opening or mouth 49. In this example, the slot 44 may be formed with a corresponding concave region, or a planar region, opposite the inwardly directed retaining portion of the sides 41 to reduce the width of the slot 44 to facilitate retention of the headgear strap 7A in the slot 44.

Although the present invention has been described in terms of certain embodiments, other embodiments apparent to those of ordinary skill in the art also are within the scope of this invention, Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A packaging insert comprising:
    an elongate support having a notional longitudinal axis, an upper part, a lower part, and opposed, spaced apart sides extending between the upper and lower parts, the elongate support further comprising at least one headgear retaining slot formed in or at each side, each at least one headgear retaining slot being elongate and comprising a width that is configured to receive and retain part of a strap of the headgear, each at least one headgear retaining slot further comprising a closed end and an open end,
    the insert further comprising at least one retaining portion, wherein each of the at least one retaining portion is inwardly directed adjacent an opening of a respective one of the at least one headgear retaining slot,
    wherein the elongate support comprises at least one indent formed in the elongate support, each of the at least one indent associated with the at least one headgear retaining slot,
    wherein each of the at least one indent forms a recess, wherein an end of the respective at least one retaining portion extends into the recess of the at least one indent, and
    wherein the end of each of the at least one retaining portion comprises an edge that is parallel to the longitudinal axis of the elongate support.

2. The packaging insert of claim 1, wherein each of the at least one retaining portion projects radially into its respective at least one headgear retaining slot.

3. The packaging insert of claim 1, wherein each of the at least one retaining portion reduces a width of its respective at least one headgear retaining slot.

4. The packaging insert of claim 3, wherein the width of the at least one headgear retaining slot is reduced adjacent the opening of the at least one headgear retaining slot.

5. The packaging insert of claim 1, wherein each of the at least one headgear retaining slot comprises a longitudinal axis that is parallel to the longitudinal axis of the elongate support.

6. The packaging insert of claim 1, wherein each of the at least one retaining portion is positioned adjacent a respective one of the at least one indent.

7. The packaging insert of claim 1, wherein each of the at least one retaining portion and respective one of the at least one indent form a circuitous path.

8. The packaging insert of claim 1, wherein each of the at least one headgear retaining slot comprises a first wall and a second wall, wherein the first wall and the second walls are not parallel.

9. The packaging insert of claim 1, wherein a width of each at least one retaining portion is increased adjacent its respective opening of the at least one headgear retaining slot.

10. The packaging insert of claim 1, wherein the elongate support comprises four headgear retaining slots and four retaining portions, each of the retaining portions is associated with a respective one of the headgear retaining slots and each of the retaining portions is inwardly directed adjacent the opening of its respective one of the headgear retaining slots.

11. The packaging insert of claim 10, wherein the elongate support comprises two headgear retaining slots and two respective retaining portions on a first side of the elongate support and two headgear retaining slots and two respective retaining portions on a second side of the elongate support.

12. The packaging insert of claim 10, wherein the elongate support comprises four indents formed in the elongate support, wherein each of the four indents is associated with one of the headgear retaining slots, and wherein an end of each one of the retaining portions extends into a respective indent.

* * * * *

UNITED STATES PATENT AND TRADEMARK OFFICE
CERTIFICATE OF CORRECTION

| | |
|---|---|
| PATENT NO. | : 11,485,562 B2 |
| APPLICATION NO. | : 17/213018 |
| DATED | : November 1, 2022 |
| INVENTOR(S) | : Erik Robertus Scheirlinck |

It is certified that error appears in the above-identified patent and that said Letters Patent is hereby corrected as shown below:

In the Specification

Column 1, Line 47, delete "patients" and insert -- patient's --.

Column 2, Line 23, below "longer considered sterile." insert -- SUMMARY --.

Column 3, Line 10, delete "my" and insert -- may --.

Column 5, Line 23, delete "of" and insert -- of an --.

Column 7, Line 58, delete "front" and insert -- from --.

Column 9, Line 4, delete "are" and insert -- arc --.

Column 9, Line 23, delete "with" and insert -- 31 with --.

Column 10, Line 29, delete "invention," and insert -- invention. --.

Signed and Sealed this
Fourteenth Day of March, 2023

Katherine Kelly Vidal
*Director of the United States Patent and Trademark Office*